United States Patent
Minakuchi et al.

[11] Patent Number: 5,957,847
[45] Date of Patent: Sep. 28, 1999

[54] METHOD AND APPARATUS FOR DETECTING FOREIGN BODIES IN THE MEDULLARY CAVITY

[76] Inventors: Yoshihisa Minakuchi, 327-4, Komatsu-cho, Koufu-shi, Yamanashi, 400; Hideki Numoto, 63-1-308, Kawanakajima, Isawa-cho, Higashiyatsushiro-gun, Yamanashi, 406, both of Japan

[21] Appl. No.: 08/913,733
[22] PCT Filed: Jan. 23, 1996
[86] PCT No.: PCT/JP96/00112
§ 371 Date: Oct. 30, 1997
§ 102(e) Date: Oct. 30, 1997
[87] PCT Pub. No.: WO97/26826
PCT Pub. Date: Jul. 31, 1997
[51] Int. Cl.[6] .................................................. A61B 8/00
[52] U.S. Cl. .......................................... 600/449; 600/459
[58] Field of Search ..................................... 600/437, 439, 600/449, 459

[56] References Cited

U.S. PATENT DOCUMENTS 3,721,227  3/1973  Larson et al. ............................ 600/461
4,819,621  4/1989  Veberle et al. ........................... 600/437
5,235,981  8/1993  Hascoet et al. .......................... 600/437

FOREIGN PATENT DOCUMENTS

| 56-58453 | 5/1980 | Japan . |
|---|---|---|
| 59-15967 | 1/1984 | Japan . |
| 62-140450 | 9/1987 | Japan . |
| 3-65681 | 3/1991 | Japan . |
| 3-280939 | 12/1992 | Japan . |
| 7-23976 | 1/1995 | Japan . |

Primary Examiner—Francis J. Jaworski
Attorney, Agent, or Firm—Hoffmann & Baron, LLP

[57] ABSTRACT

An apparatus for detecting a lateral locking hole of an intramedurally nail includes a targeting device. The targeting device has a support lever having a slider attached thereto. An ultrasonic probe is mounted at an lower end of the support lever. An ultrasonic wave is transmitted and received by a transceiver of the ultrasonic probe while moving the slider in a direction perpendicular to an axis of the intramedullary nail by a screw. The lateral locking hole of the intramedullary nail is detected of position by a height of echo of the ultrasonic wave.

8 Claims, 15 Drawing Sheets

METHOD AND APPARATUS FOR DETECTING FOREIGN BODIES IN THE MEDULLARY CAVITY

FIELD OF ART

This invention relates generally to methods and apparatuses for detecting a foreign body existing within a medullary cavity. More particularly, this invention relates to a method and apparatus adapted to detect a lateral locking hole formed in an intramedullary nail inserted within a medullary cavity. For example, when conducting an osteosynthetic operation to mend a fractured bone, an intramedullary nail is inserted inside a bone medulla and thereafter a lateral locking hole of the intramedullary nail is detected to thread thereinto a thread screw for fixation between the bone and the intramedullary nail.

PRIOR ARTS

The osteosynthetic methods for mending a fractured bone involve one method that merely implants an intramedullary, or bone, nail within a medulla to fix the bone. There exists another method of fixing an intramedullary nail to a bone, wherein a hole is opened in a bone by drilling from the above of a skin in a manner aiming at a lateral locking hole of an intramedullary nail implanted within a medulla in order to thereby fix a thread screw between the bone and the intramedullary nail.

In the latter case, a targeting device 1 (illustrated by an apparatus manufactured by ACE Company) as shown in FIG. 18 and FIG. 19 is utilized. With the targeting device 1, an X-ray 2 is radiated to a lateral locking hole 4 of an intramedullary nail 3 so as to monitor by X-ray imaging the lateral locking hole, or otherwise the location of a lateral locking hole is determined in a freehand manner under transillumination by an X-ray. Specifically, the ACE-make apparatus of FIG. 19 adopts a method that a guide sheath 6 is allowed to slide in a direction perpendicular to an axis of a femur 7 (FIG. 8) so that the guide sheath 6 can be fixed in position by means of a screw 8 (8').

With such targeting device 1, the amount of X-ray exposure is lessened and the fixation of the thread screw to the intramedullary nail is simplified, as compared with the conventional case where a lateral locking hole is located in a freehand manner under X-ray transillumination.

However, the utilization of the targeting device 1 is less successful, despite a reduced amount of exposure as compared to the method of determining the position of a lateral locking hole in a freehand manner under X-ray transillumination. This is because the guide sheath 6 provided at an end portion of the targeting device 1 is apt to delicately deviate relative to the location of the lateral locking hole after inserting the intramedullary nail 3 into the medulla. It is considered the cause of this deviation is attributable to a curvature in the intramedullary nail 3 due to a curvature in the femur or a flexure in the targeting device 1. Note that it is to be considered that expansion, shrinkage, and twist in the intramedullary nail 3 is negligible. Meanwhile, there also exists an extremely significant health problem caused by X-ray exposure 2 to a patient in the present and the future as well as the exposure to hands of a doctor who conducts many operations. In particular, the operation of detecting a location of an intramedullary nail from the above the skin requires several minutes of X-ray radiation for locating one hole (usually at two locations). Therefore, a great amount of X-ray exposure occurs not only to the doctor but also the patient. Under such situations, a demand exists for a surgical method that is free from the worry of X-ray exposure.

SUMMARY OF THE INVENTION

It is therefore a primary object of the present invention to provide a method and apparatus which is capable of detecting a foreign body, such as of a metal or a ceramic, within a bone medullary cavity, in a manner free from ray exposure.

It is another object of the present invention to provide a method and apparatus that can detect the position of a lateral locking hole of an intramedullary nail in a manner free from ray exposure.

A method for detecting a foreign body within an intramedullary cavity according to the invention, comprises the following steps: (a) scanning an ultrasonic wave signal in a direction perpendicular to an axis of an intramedullary cavity; and (b) detecting a foreign body based on a height of an ultrasonic wave echo.

Also, an apparatus for detecting a foreign body within an intramedullary cavity according to the invention, comprises: an ultrasonic probe; and a scanning means for scanning an ultrasonic wave signal emitted from the ultrasonic probe in a direction perpendicular to an axis of an intramedullary cavity, whereby a foreign body is detected based on echo obtained by the ultrasonic probe.

A method for detecting a lateral locking hole of an intramedullary nail inserted within a medullary cavity according to the invention, comprises the following steps: (a) scanning with an ultrasonic wave signal in a direction perpendicular to an axis of an intramedullary nail; and (b) detecting a lateral locking hole based on a height of an ultrasonic wave echo.

An apparatus for detecting a lateral locking hole of an intramedullary nail implanted within a medullary cavity, comprises: an ultrasonic probe; and a scanning means for scanning with a signal of an ultrasonic wave emitted from the ultrasonic probe in a direction perpendicular to an axis of an intramedullary nail, whereby the lateral locking hole is detected based on an echo obtained from the ultrasonic probe.

The ultrasonic wave propagates through muscles, bones and medulla. Moreover, there is a large difference in acoustic impedance between the medulla and the intramedullary nail that is generally formed of a metal. Consequently, an ultrasonic wave transmitted is to be well reflected by the intramedullary nail, to be received by the ultrasonic probe in an echo form with clarity. To this end, it is possible to determine the location of an intramedullary nail with high accuracy.

Since, in the present invention the state of a foreign body, such as of a metal or a ceramic, existing within a medullary cavity is detected by the utilization of echo of an ultrasonic wave signal, there is no possibility of radiation exposure to a medical doctor or a patient. Even when detecting a lateral locking hole of an intramedullary nail, it is possible to grasp the location thereof with higher accuracy without suffering from radiation exposure as compared to the conventional apparatus using an X-ray. This in turn makes possible attachment, at an accurate position, of a thread screw to fix the intramedullary nail inserted within a medulla, enhancing accuracy of surgical operation and thus reducing the time required for this operation.

The above described objects and other objects, features, aspects and advantages of the present invention will become more apparent from the following detailed description of the present invention when taken in conjunction with the accompanying drawings.

PREFERRED EMBODIMENT FOR PRACTICING THE INVENTION

Figure 1:
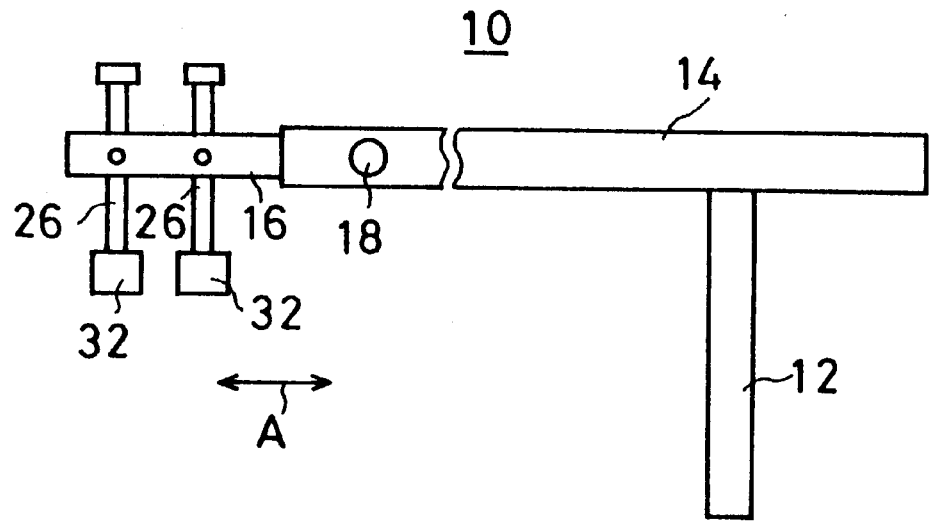
FIG. 1 is an illustrative side view showing a targeting device employed in an embodiment of the present invention.
Figure 3:
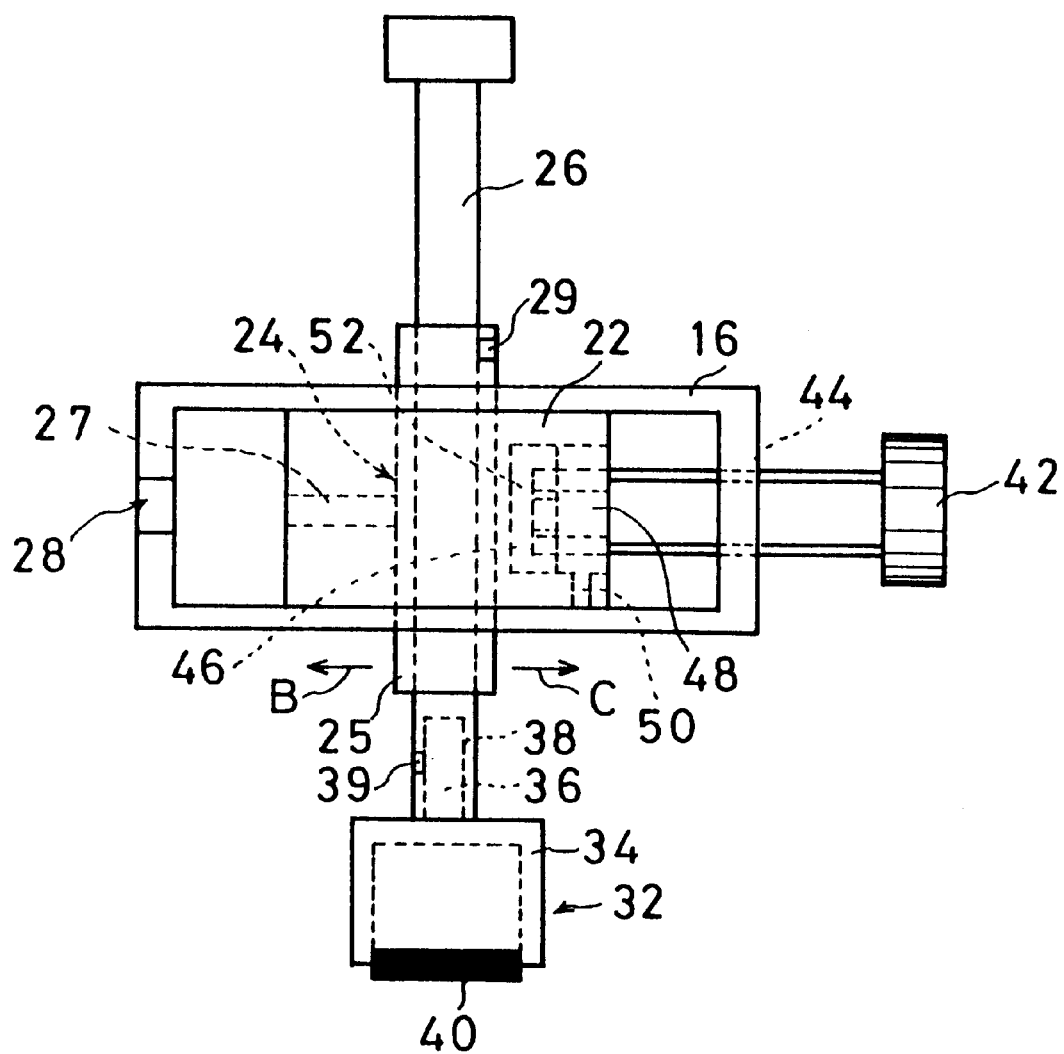
FIG. 3 is an illustrative view showing in detail the tip end portion of the targeting device.

In embodiments according to the invention, a targeting device 10 as shown in FIG. 1 and FIG. 3 which is constructed similarly to the conventional apparatus is used. The targeting device 10 is placed in setting such that a horizontal surface thereof is always perpendicular to the direction of a lateral locking hole 4 of an intramedullary nail 3, i.e. the direction of screw insertion.

Incidentally, an embodiment will be shown hereinbelow wherein the present invention is applied to a method and apparatus for detecting a lateral locking hole of an intramedullary nail existing as a foreign body within a medullary cavity. However, it should be pointed out beforehand that this invention is not limited to such an embodiment but can also be adapted broadly to detect foreign bodies within an intramedullary cavity involving, for example, the state of a metal or ceramic member, etc., the number of foreign bodies, the depth, the size (length and thickness), and so on.

Figure 18:
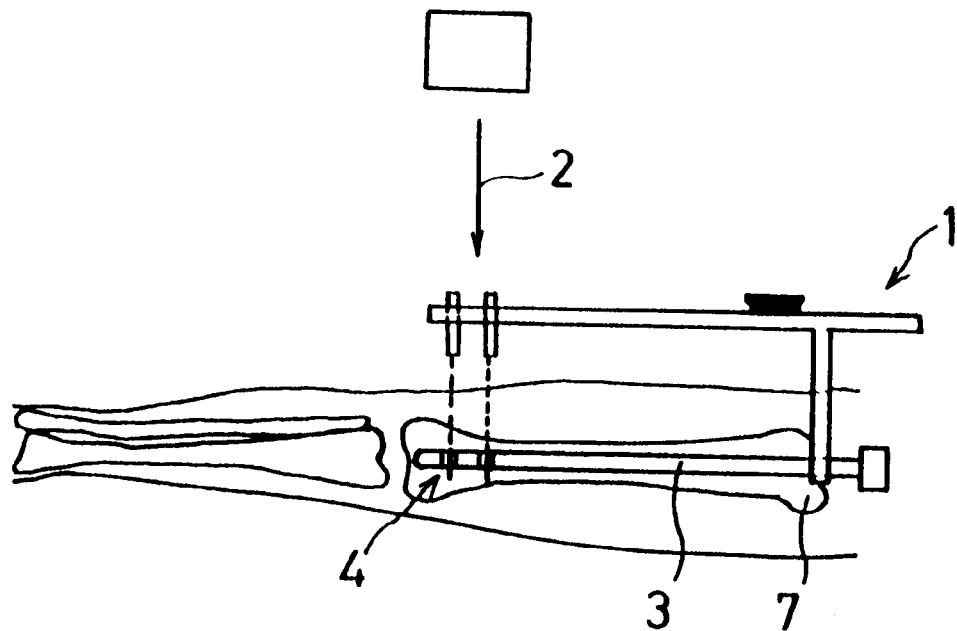
FIG. 18 is an illustrative view showing one example of a conventional targeting device.
Figure 19:
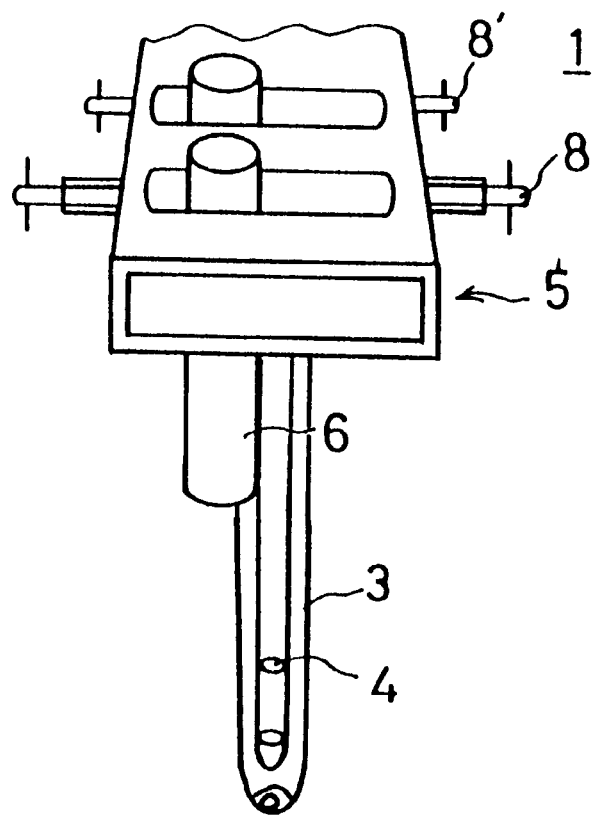
FIG. 19 is an illustrative view showing by magnification the end portion of a conventional targeting device.

In the embodiment, the targeting device 10 includes a support lever 12 to be fixed to an intramedullary nail 3 (FIG. 18). The support lever 12 has a top end fixed with a first hollow lever 14 that is, for example, in rectangular in section. This first hollow lever 14 has a second hollow lever 16 slidably received therein so that the second hollow lever 16 can slide to be extended and retracted along an inside of the first hollow lever 14. The second hollow lever 16 is fixed at an expanded or retracted position relative to the first hollow lever 14 by a screw 18 provided penetrating through a side surface of the first hollow lever 14 to have a tip end abutting against a side surface of the second hollow lever 16.

Figure 2:
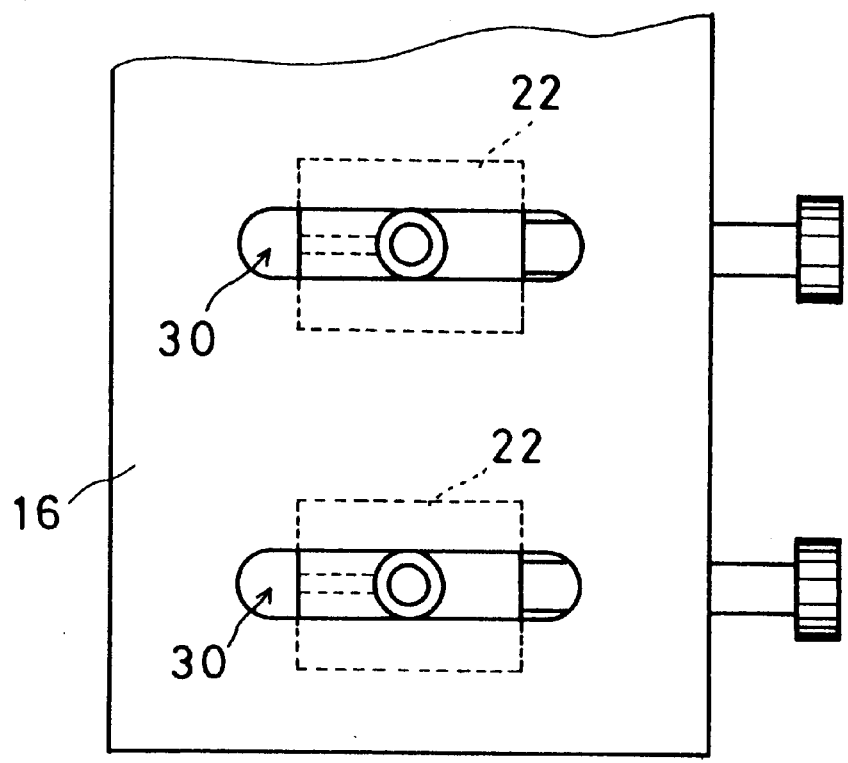
FIG. 2 is an illustrative plan view showing by magnification a tip end portion of the targeting device.

The second follow lever 16 has sliders 22 incorporated into the vicinity of a tip end thereof, as can be well understood particularly in FIG. 2 and FIG. 3. The slider 22 is formed with a through-hole 24 so that this through-hole 24 has a cylindrical guide lever 25 inserted therethrough. The guide lever 25 is fixed by a set screw 27. Incidentally, the set screw 27 is turned by a screw driver or the like inserted through a hole 28 formed through a side face of the second hollow lever 16. The guide lever 25 has a support lever 26 inserted therethrough so that the support lever 26 is fixed to the guide lever 25 through a set screw 29. The support lever 26 has its upper and lower ends respectively projecting upward and downward of the second hollow lever 16 through elongate holes 30 formed correspondingly in an upper and lower surface of the second hollow lever 16. The support lever 26 is mounted at its lower end with an ultrasonic probe 32. More specifically, the ultrasonic probe 32 has its case 34 as shown in FIG. 3. The case 34 has a convex portion 36 formed at a top surface thereof, which convex portion is received in a concave portion 38 formed at a lower end of the support lever 26 so that these two portions are fixed through a set screw 39. In this manner, the case 34 is detachably mounted on the support lever 26. The ultrasonic probe 32 mounted on the case 34 includes a ultrasonic wave transceiver 40. Consequently, when the slider 22 is moved in a direction of the arrow B or C in FIG. 3 by the screw 42, the ultrasonic probe 32 responds and moves in the same direction.

The screw 42, that is arranged for moving the slider 22 in the direction of the arrow B or C, is inserted to the inside of the second hollow lever 16 through a thread hole 44 formed in a side surface of the second hollow lever 16. This screw 42 has a tip rotatably attached to a concave portion 46 of the slider 22. That is, the concave portion 46 is mounted with a bearing 48 which is capable of bearing axial loads so that an outer race of the bearing 48 is fixed by a set screw 50. The screw 42 at its tip faces the concave portion 46, which tip end is fixed to an inner race of the bearing 48 for example through a nut 52. Consequently, if the screw 42 is rotated, the tip end thereof is displaced in the direction of the arrow B or C and the inner race of the bearing 48 is rotated responsive thereto, thereby displacing the slider 22. In this manner, the ultrasonic probe 32 is moved in the direction of the arrow B or C to be positioned in position by rotating the screw 42. The second hollow lever 16 is placed extending in the axial direction of the femur 7 shown in FIG. 18 with the result that the ultrasonic probe 32 can be moved or displaced in a direction perpendicular to the femur 7, i.e. to the axis of the intramedullary nail 3.

Figure 4:
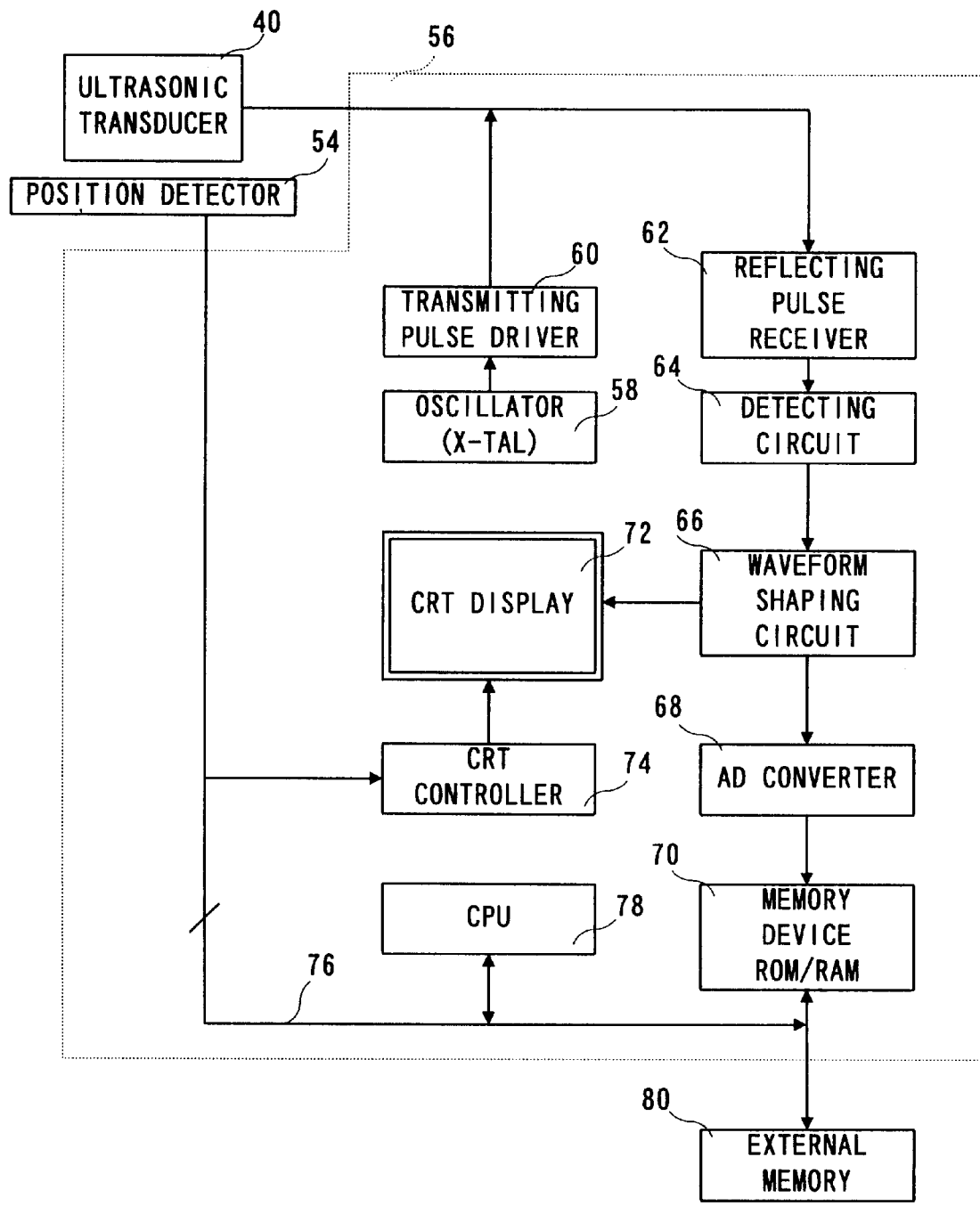
FIG. 4 is a block diagram showing one embodiment of a detecting circuit for detecting a lateral locking hole of an intramedullary nail by using an ultrasonic wave signal obtainable from the targeting device.

The above-mentioned screw 42 is coupled to a position detector 54 given in FIG. 4. The position detector 54 generates a pulse signal by, for example, the rotation of the screw 42, and outputs data representative of a position of the screw 42, i.e., a position of the ultrasonic probe 32 through measurement on the pulse signal. This position detector 54 together with the ultrasonic wave transceiver 40 included in the ultrasonic probe 32 is connected to a detecting circuit 56.

More specifically, the ultrasonic transceiver 40 is supplied with a transmitting pulse, which transmitting pulse is outputted from a transmitting pulse driver 60 depending upon a signal supplied from an oscillator 58. That is, the oscillator 58 is constituted, for example, as a crystal oscillator so as to generate a pulse signal having a repetition period attainable an oscillation frequency of the ultrasonic transceiver 40. This pulse signal is supplied to the transmitting pulse driver 60. The transmitting pulse driver 60 makes amplification on the same pulse signal to generate a transmitting pulse voltage so that the transmitting pulse voltage can be applied to the ultrasonic transceiver 40. The ultrasonic transceiver 40 generates an ultrasonic pulse in response to the transmitting pulse voltage. This ultrasonic pulse is radiated to the femur 7, i.e. to the intramedullary nail 3, as stated above.

On the other hand, the radiation of the ultrasonic pulse causes a reflecting pulse (echo), which is converted into an electric signal by the ultrasonic transceiver 40. The echo signal is amplified by the reflecting pulse receiver 62, and then the waveform is detected by a waveform detecting circuit 64. The echo detected by the waveform detecting circuit 64 is shaped in waveform by a waveform shaping circuit 66, and then converted by an A/D converter 68 into digital data representative of a level of the echo. This echo height data is memorized by a RAM in a memory device 70. This echo signal waveform-shaped by the waveform shaping circuit 66 is inputted also to a CRT display 72 so that the waveform thereof is displayed on the CRT. Incidentally, this CRT display 72 is controlled, like an oscilloscope, by a CRT controller 74. That is, the positional data from the above-mentioned position detector 54 is inputted through a bus 76 to the CRT controller 74 so that the abscissa on the CRT display 72 is prescribed by the positional data.

Further, the CRT controller 74 and the memory device 70 are coupled to a CPU 78 via the bus 76 so that they can be controlled by the CPU 78. The positional data and the echo height data stored by the memory device 70 are appropriately dealt with by the CPU 78, and again stored into the memory device 70. The data processed is then recorded, as required, by an external memory 80 such as a magnetic tape, a hard disc or a magnetooptic disc.

Explanation will now be made for a method for detecting a lateral locking hole of an intramedullary nail with reference to FIG. 5 and FIG. 6 as well as FIG. 7 and FIG. 8, wherein the detection is done through the ultrasonic probe 32 and the detecting circuit 56 by using the targeting device 10 constructed as stated above.

Figure 5:
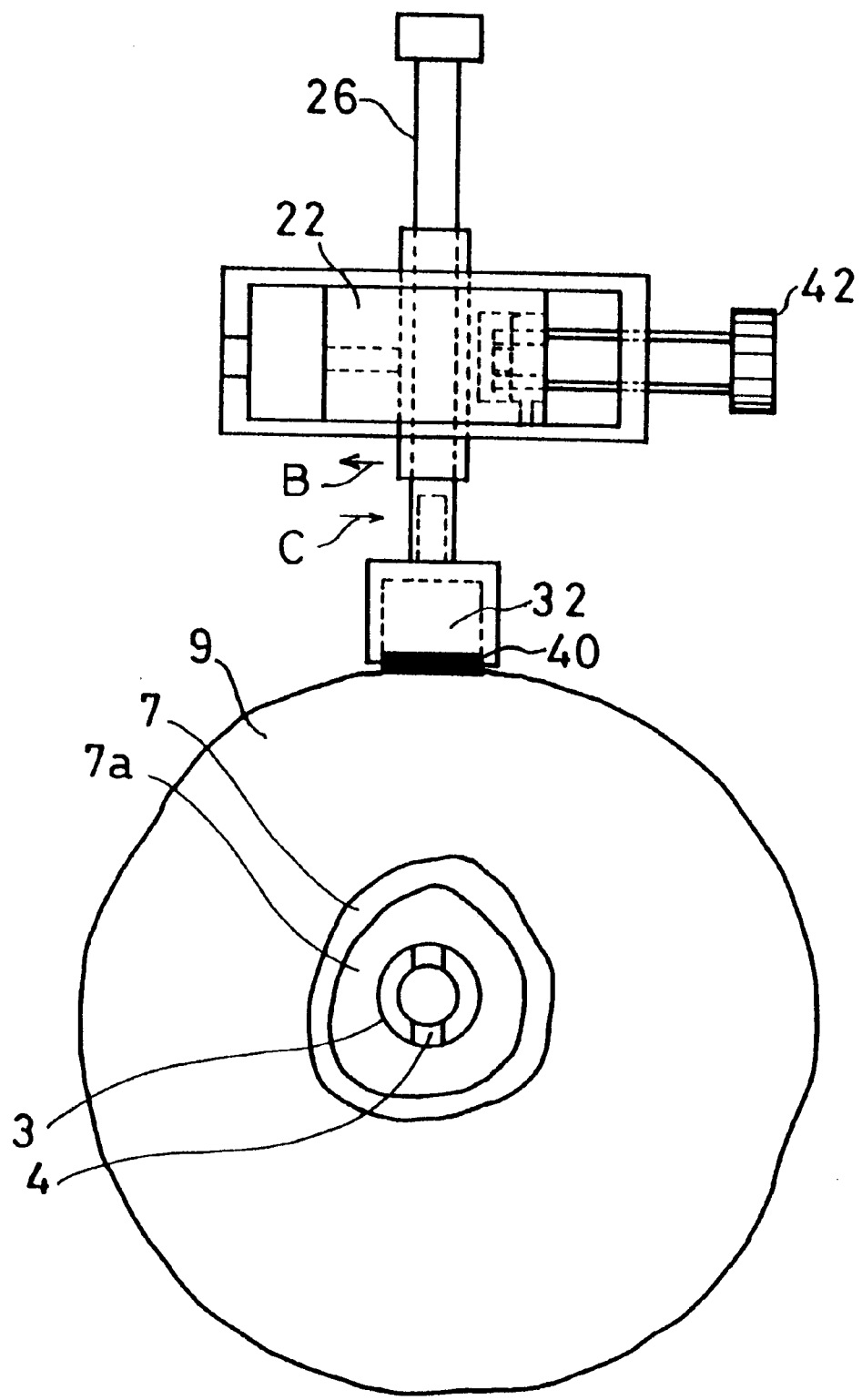
FIG. 5 is an illustrative view showing one example wherein a lateral locking hole is detected of position by scanning an ultrasonic signal by using the targeting device shown in FIG. 1–FIG. 3.

An intramedullary nail 3 is inserted within a medulla 7a of a femur 7, and then the targeting device 10 is placed such that the second hollow lever 16 assumes a plane perpendicular to the lateral locking hole 4 of an intramedullary nail 3 as shown in FIG. 5. An ultrasonic probe 32 is mounted to the tip portion of the support lever 26 of the targeting device 10. An acoustic coupling agent, for example, of Sonojelly (commodity name: Toshiba Medical Co., Ltd.) is applied between the transceiver 40 of the ultrasonic probe 32 and a skin of thigh muscle, through which an ultrasonic wave is incident upon the lateral locking hole 4 of the intramedullary nail from the above of the skin. The ultrasonic probe 32 is on a plane perpendicular to the intramedullary-nail lateral locking hole so that the ultrasonic probe 32 is slid by the screw 42 in a direction perpendicular to the axis of the femur 7 (Z-axis direction), i.e. in the direction of the arrow B or C. At this time, the ultrasonic wave is transmitted through the femur to cause an echo reflecting from or around the intramedullary-nail lateral locking hole 4 in a manner responsive to the displacement or movement of the ultrasonic probe 32. The echo height is measured by the CRT display 72, etc. to determine the location of the lateral locking hole 4. Incidentally, the detecting method for an intramedullary-nail lateral locking hole is different due to an incident state of an ultrasonic beam from the ultrasonic probe 32.

Figure 6:
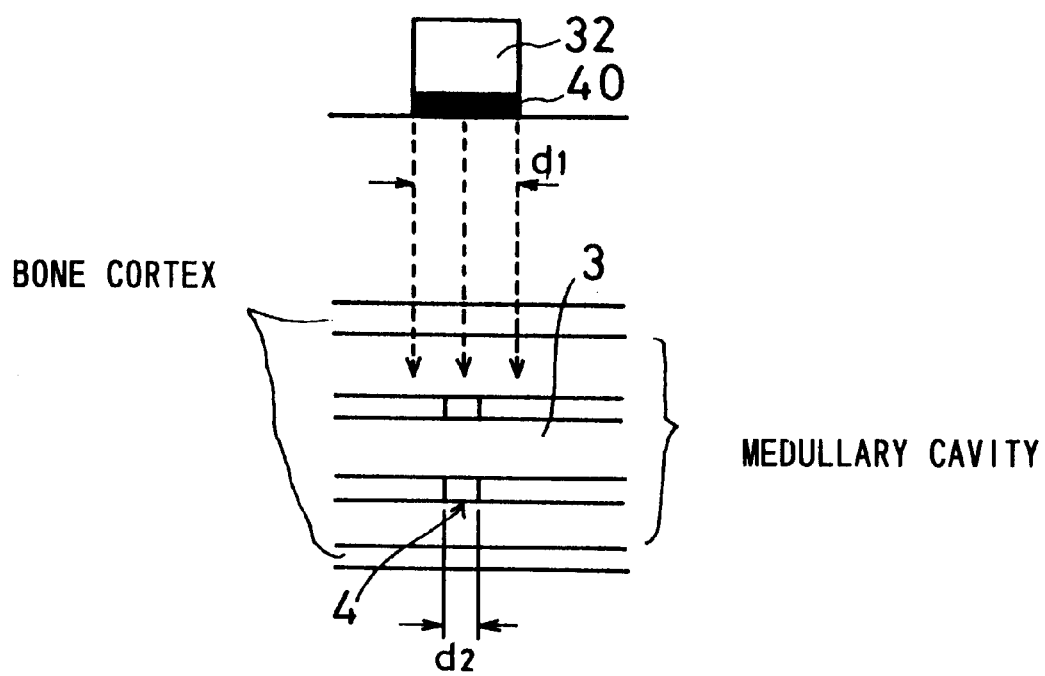
FIG. 6 is an illustrative view showing the relationship, in the case of FIG. 5, between the size d1 of an ultrasonic transceiver and the diameter of the lateral locking hole.

FIG. 5 and FIG. 6 show a case where the intramedullary nail 3 is circular or a curved surface in section to have a lateral locking hole 4 through which a screw is passed, wherein the size d1 of the oscillator or transceiver 40 of the ultrasonic probe 32 is greater than the diameter d2 of the lateral locking hole 4. In this case, if the ultrasonic probe 32 is moved by the screw 42 in the Z-axis direction perpendicular to the axis of the femur 7, i.e. in the direction of the arrow B or C, the height of the echo is initially zero but increases as the position Z=0 (immediately above the lateral locking hole 4) is approached. The echo height reaches its maximum at Z=0 and thereafter decreases to zero. In this manner, when the ultrasonic probe 32 is scanned or moved by the screw 42, the echo height attains its maximum at the position Z=0, i.e., at the center of the lateral locking hole 4.

Figure 7:
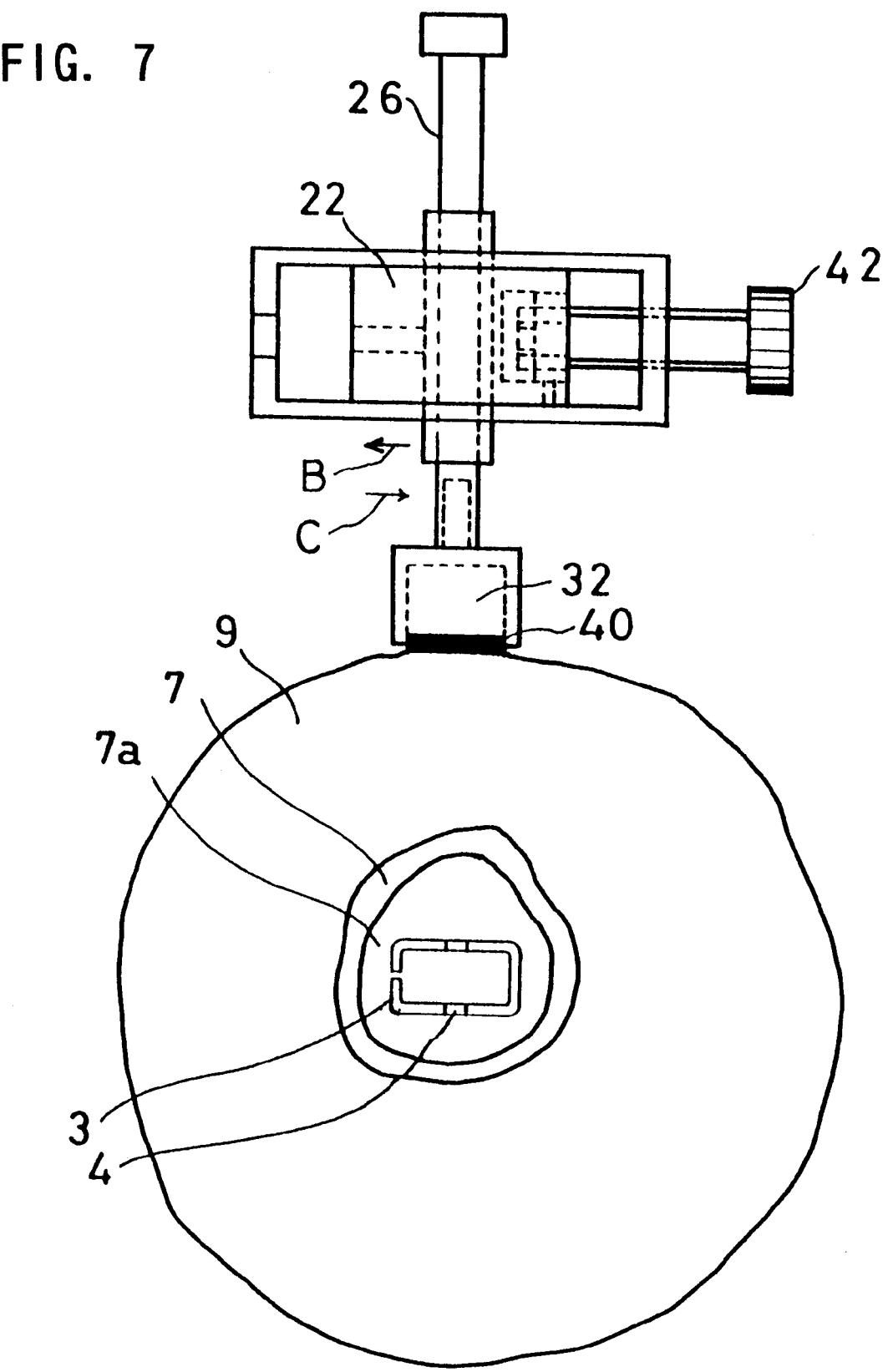
FIG. 7 is an illustrative view of another example showing that the lateral locking hole is detected of position by scanning an ultrasonic signal by using the targeting device shown in FIG. 1–FIG. 3.
Figure 8:
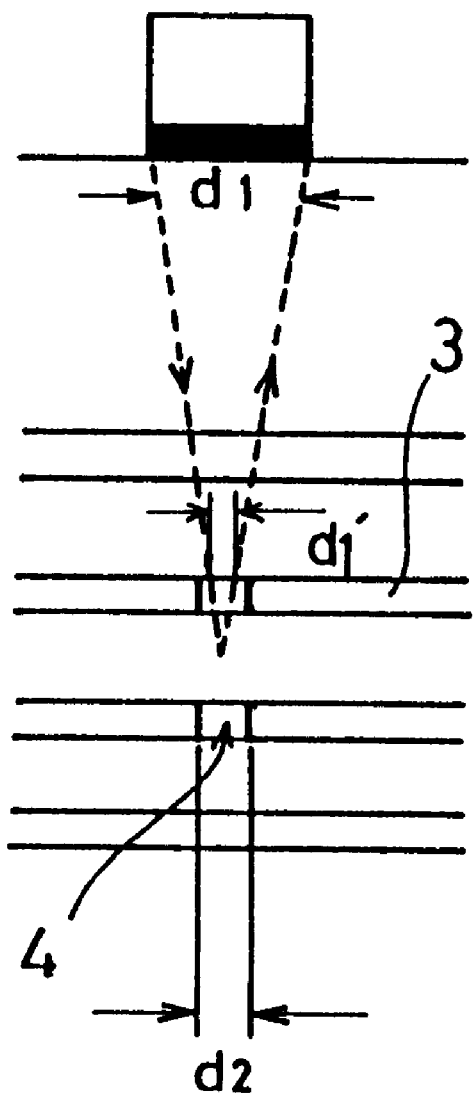
FIG. 8 is a diagram showing the relationship, in the case of FIG. 7, between the size d1 of the ultrasonic transceiver and the diameter d2 of the lateral locking hole.

On the other hand, FIG. 7 and FIG. 8 show a case that the intramedullary nail 3 is in a squared-U shape in section to have a flat surface around its lateral locking hole 4 through which a screw is passed, wherein the size d1 of the transceiver 40 of the ultrasonic probe 32 is smaller than the diameter d2 of the lateral locking hole 4. Or, the case may be that the size of the transceiver 40 is greater than that of the lateral locking hole, but the ultrasonic beam is focussed so that the size d1 thereof reaching around the lateral locking hole is smaller than the diameter d2 of the lateral locking hole 4. In this case, if the ultrasonic probe 32 is moved in the direction perpendicular to the axis of the femur 7, i.e. in the Z-axis direction, the echo height is initially zero, but it increases as the position Z=0 (immediately above the lateral locking hole 4) is approached. However, as the position Z=0 is further approached, the echo height becomes lower. When the ultrasonic probe 32 comes to a position at which the ultrasonic beam in its size is receivable within the lateral locking hole 4, the echo height disappears completely. Thereafter, when the ultrasonic probe 32 is further moved in the Z-axis direction, the echo begins to reoccur and then again disappear. In this manner, the position at which the echo height disappears has its center located at Z=0, i.e. the central point of the lateral locking hole 4.

The echo is not obtained where the intramedullary nail 3 is circular or of a curved surface in section as shown in FIG. 5 and FIG. 6 to have a lateral locking hole 4 through which a screw is passed, wherein the size of the transceiver 14 of the ultrasonic probe 32 is smaller than the diameter of the lateral locking hole 4. The echo is also not obtained where the size of the transceiver 40 is greater than that of the lateral locking hole but the ultrasonic wave beam is focussed such that the size thereof reaching around the lateral locking hole 4 is smaller than the lateral locking hole. However, even where the section in shape around the lateral locking hole 4 has a curved surface approximated to a flat plane, the echo if received has a level presenting in principle a tendency similar to that of the case shown by FIG. 7 and FIG. 8.

Incidentally, when the ultrasonic probe 32 shown in FIG. 5 and FIG. 6 is employed and the intramedullary nail 3 is in a flat surface form in section as shown in FIG. 7, the point that the echo level reaches its maximum correspond to the center of the lateral locking hole 4.

Figure 10:
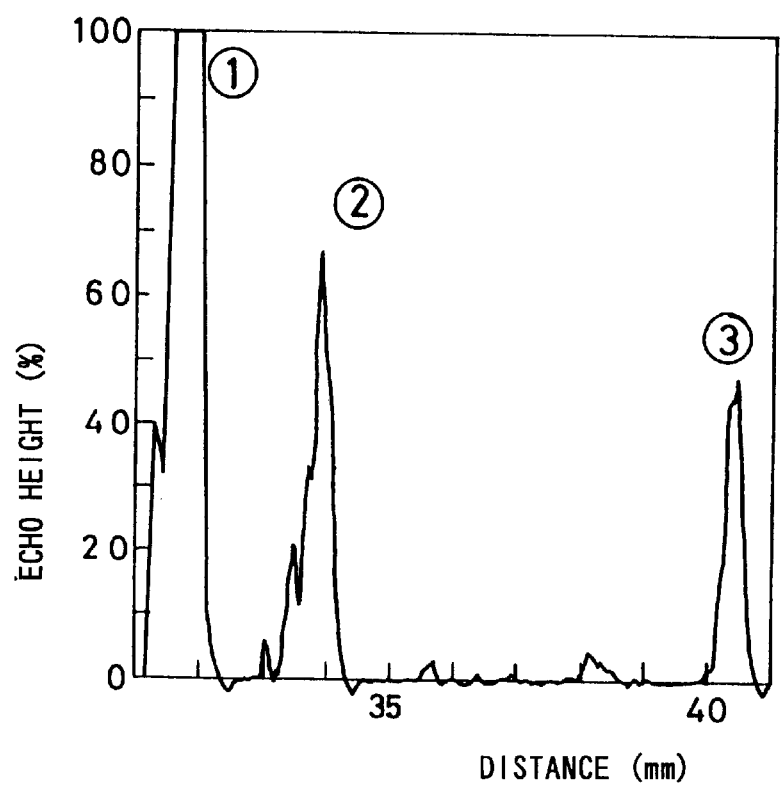
FIG. 10 is an illustrative diagram showing an echo waveform at a position Z=1.5 mm in the experiment of FIG. 9.

The present inventors have conducted experiments given hereinbelow to verify the practicability for the above embodiments. In the experiments, a hog thigh bone was cut into round slices of a length of approximately 30 mm to prepare a bone piece. The bone piece was attached on one end surface side with a rubber plate having a thickness of 10 mm. An intramedullary nail 3 of a diameter of 5 mm having a lateral locking hole 4 of a diameter of 5 mm was inserted through a center of the rubber plate. This specimen was submerged in water at a temperature of 8° C. The sample was placed such that the ultrasonic probe at its transceiver surface (13 mm in diameter) is immersed in water in a manner securing a distance of 40 mm from the transceiver surface to the intramedullary nail. Ultrasonic waves were radiated incident upon the sample. By moving the ultrasonic probe in the Z-axis direction at an interval of 0.5 mm, a measurement was made of the height of echo that was obtained, among boundary planes different in acoustic impedance, from around the 5.5 mm-diameter intramedullary-nail lateral locking hole. In this experiment, the echo as shown in FIG. 10 was observed at a position, as one example, of Z=1.5 mm. In FIG. 10, ① denotes an echo from an outside of the femur, ② an echo from an inside of the femur, and ③ an echo from the vicinity of the intramedullary-nail lateral locking hole 4. Therefore, the lateral locking hole can be detected by observing the level of the echo shown by ③.

Figure 9:
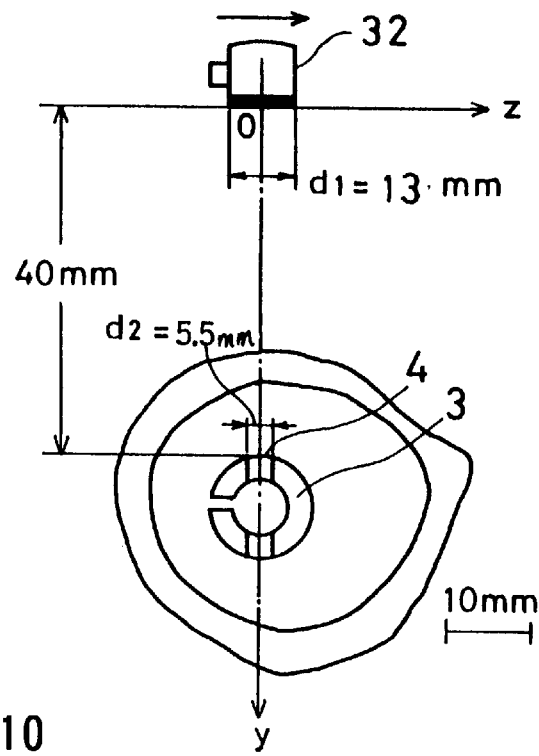
FIG. 9 is an illustrative view showing an example of an experiment conducted by the inventors, et al.
Figure 11:
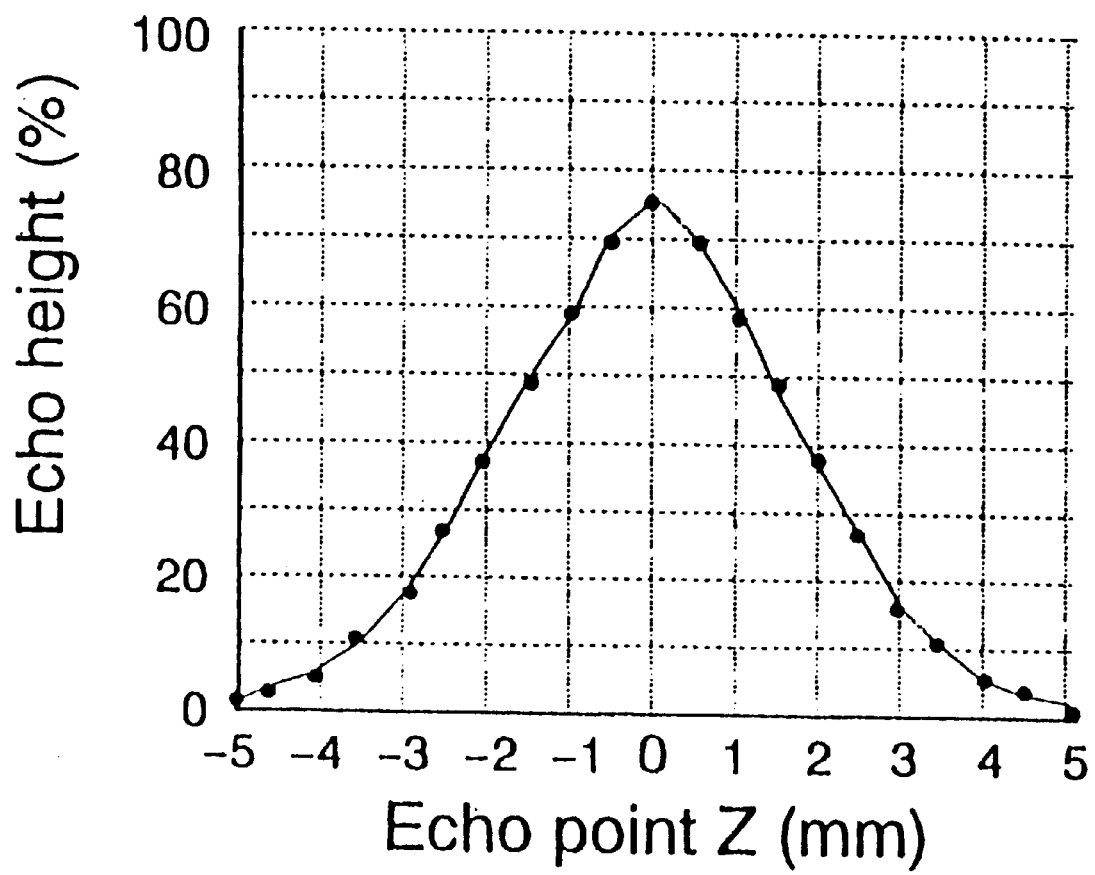
FIG. 11 is a graph showing the intensity of the echo with respect to the Z-axis position where d1>d2 is given in the experiment shown in FIG. 9.

In the experiment shown in FIG. 9, when d1>d2 is set as shown in FIG. 6, the echo height as shown in FIG. 11 is obtained for the vicinity of the intramedullary-nail lateral locking hole 4. That is, the position Z=0 mm corresponds to an uppermost point (top) in a cylindrical portion of the intramedullary nail. Consequently, it is understood from FIG. 11 that the echo height reaches its maximum at the uppermost point in the cylindrical portion of the intramedullary nail. That is, the position that the echo level reaches its maximum falls on the center point of the intramedullary-nail lateral locking hole.

Figure 12:
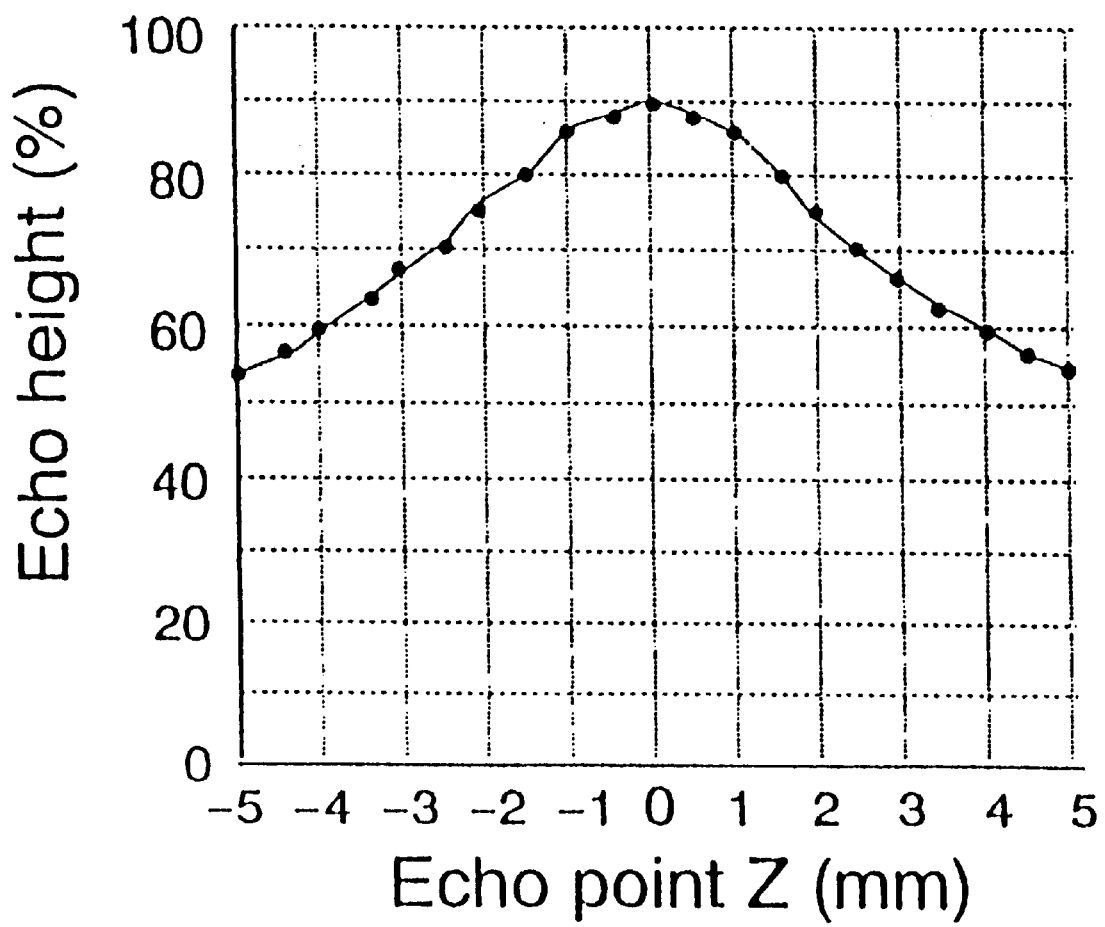
FIG. 12 is a graph showing the intensity of the echo with respect to the Z-axis position, where the intramedullary nail of FIG. 7 is used with d1>d2 given in the experiment shown in FIG. 9.

In the experiment shown in FIG. 9, when the intramedullary nail shown in FIG. 7 is employed and further d1>d2 is set as shown in FIG. 6, the echo height is obtained as shown in FIG. 12. That is, the position Z=0 mm corresponds to the center point of the intramedullary-nail lateral locking hole.

Figure 13:
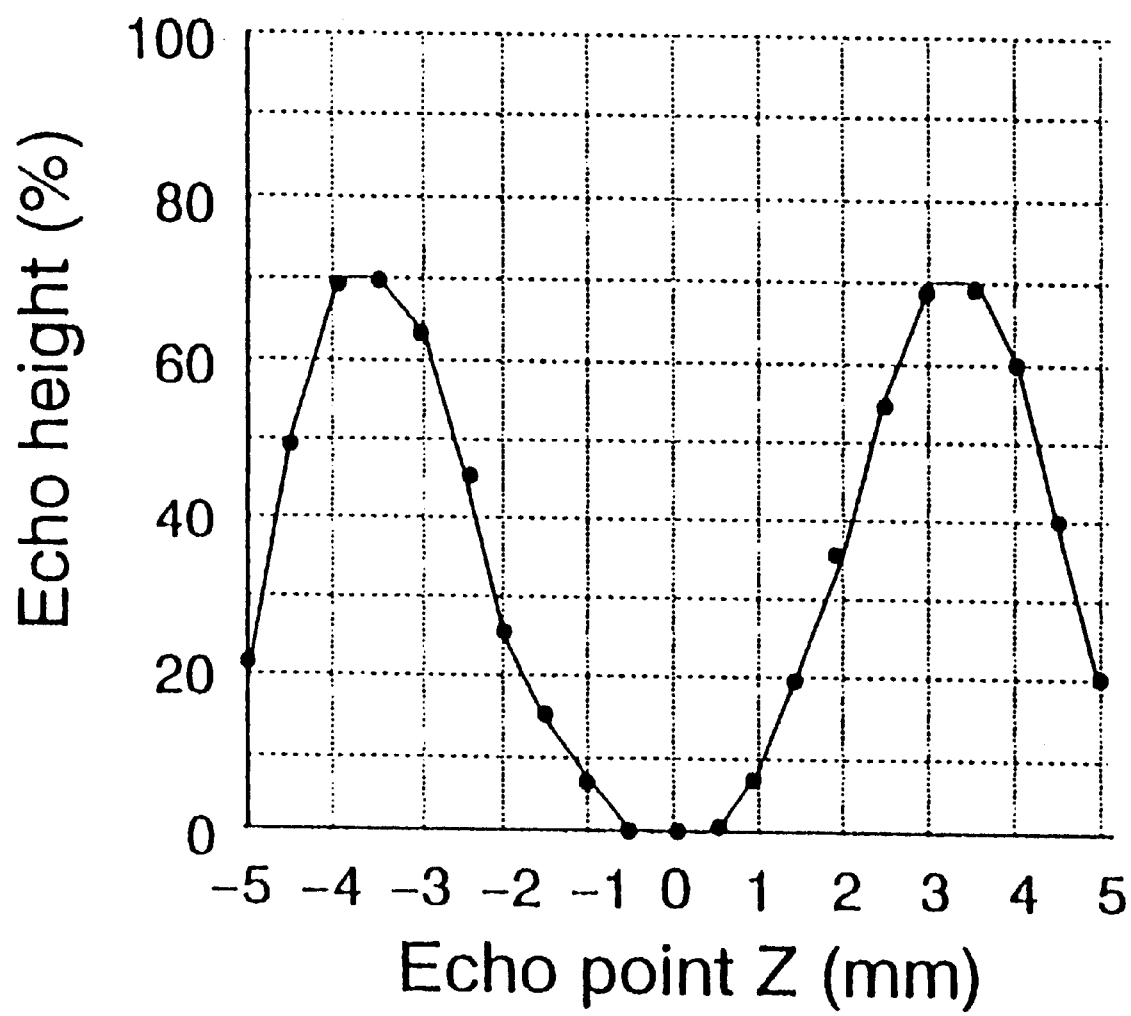
FIG. 13 is a graph showing the intensity of the echo with respect to the Z-axis position where the intramedullary nail of FIG. 7 is used with d1<d2 given in the experiment shown in FIG. 9.

Further, in the experiment shown in FIG. 9, when the intramedullary nail shown in FIG. 7 is employed with d1 (or d1')<d2 set as shown in FIG. 8, the echo height as shown in FIG. 13 is obtained for the vicinity of the intramedullary-nail lateral locking hole 4. In this case, the echo level almost reaches zero at the position of the lateral locking hole 4. Therefore, the position at which the echo height is zero lying between the maximum echo level portions represents the position of the intramedullary-nail lateral locking hole 4.

After locating the position by using the ultrasonic wave in this manner, the support lever 26 and the ultrasonic probe 32 mounted thereon are removed from the targeting device 10. In this position, a hole is formed open in the bone by drilling through the guide level 25 from the above of the skin in a manner aiming at the femur and the intramedullary-nail lateral locking hole. Thereafter, the femur and the intramedullary nail are fixed therebetween through a thread screw. It can be understood that at the position of the lateral locking hole is to be measured with accuracy so as to laterally lock the intramedullary nail by the surgical method stated as above.

Figure 14:
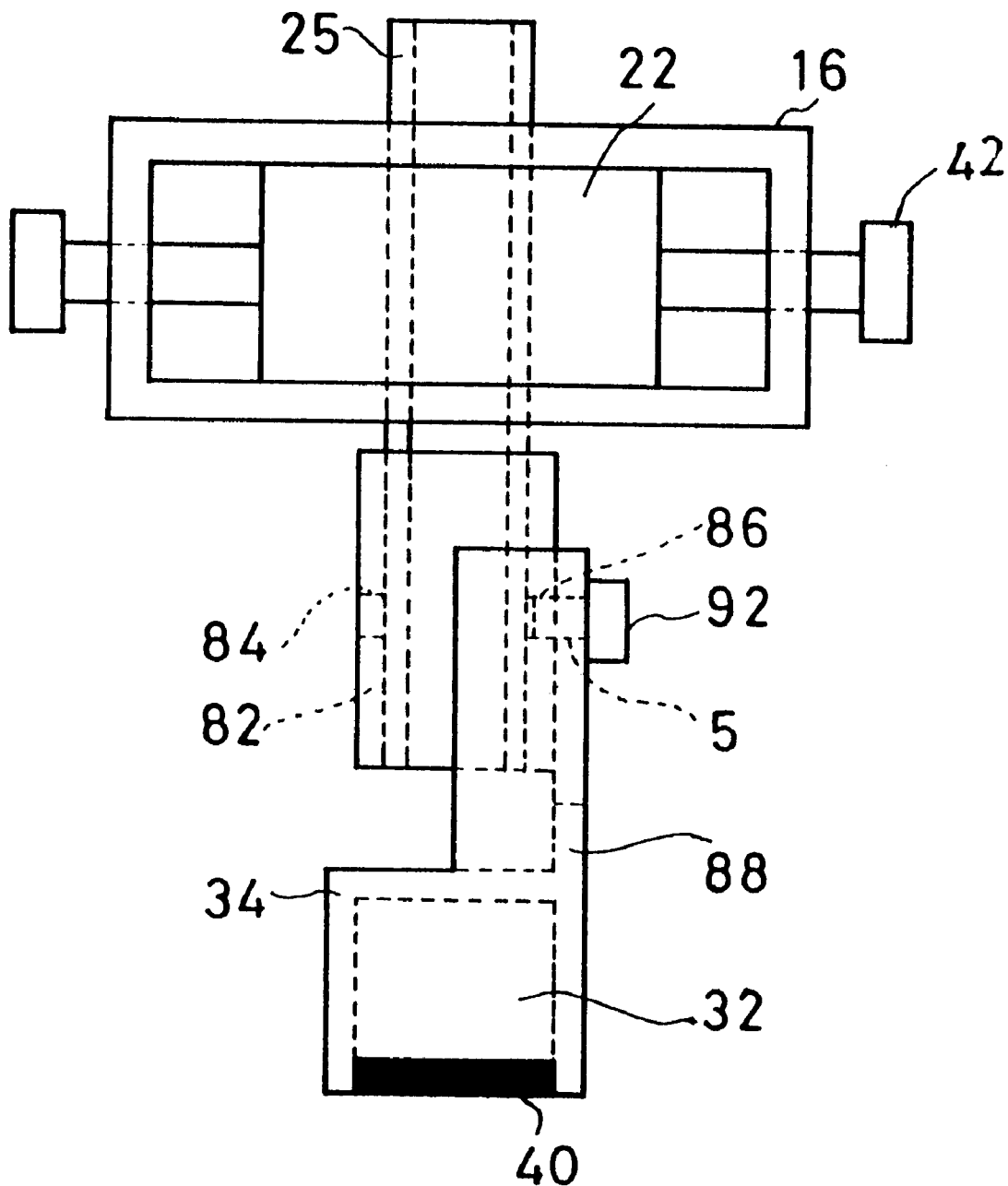
FIG. 14 is an illustrative view showing another example of a structure of the mounting with the ultrasonic probe on the targeting device.
Figure 15:
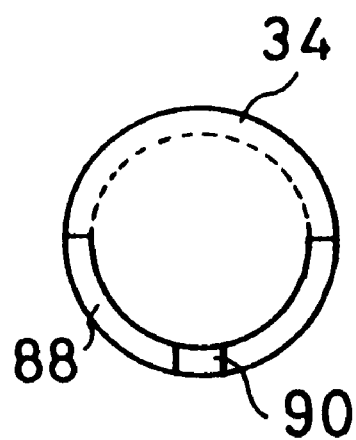
FIG. 15 is an illustrative plan view showing a plate in the FIG. 14 embodiment.
Figure 16:
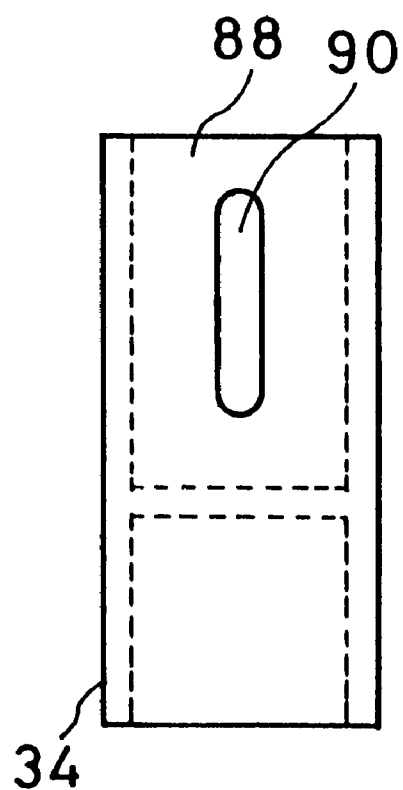
FIG. 16 is an illustrative side view showing the plate in the FIG. 14 embodiment.

Incidentally, the ultrasonic probe 32 may be attached to the guide lever 25 as shown in FIG. 14–FIG. 16, in place of the above embodiment. That is, a cylindrical member 82 is further fitted over the guide level 25 inserted through the slider 22 provided within the second hollow lever 16. This cylindrical member 82 is fixed to the guide lever 25 by a set screw 84. Although the ultrasonic probe may be directly attached to the guide lever 25 by a screw, in such a case the screw reaches an inside of the guide level 25 and accordingly there is a possibility of an inconvenient problem caused by "cuttings" or the like left at a tip of the screw. In order to avoid this, the present embodiment employs the cylindrical member 82 which is fixed on the guide lever 25 through the set screw 84.

The cylindrical member 82 is further formed with a threaded hole 86, and the case 34 for the ultrasonic probe 32 has a semi-cylindrical plate 88 extending upward therefrom to have an elongate hole 90 in the plate 88. By inserting a set screw 92 in the threaded hole 86 from the outward of the plate 88 through the elongate hole 90, the plate 88 or the case 34 (ultrasonic probe 32) can be detachably attached to the cylindrical member 82 or the guide lever 25. Note that the ultrasonic probe 32 is adjustable in vertical position through the elongate hole 90. The plate 88 or the ultrasonic probe 32 can be dismounted by removing the set screw 92.

Figure 17:
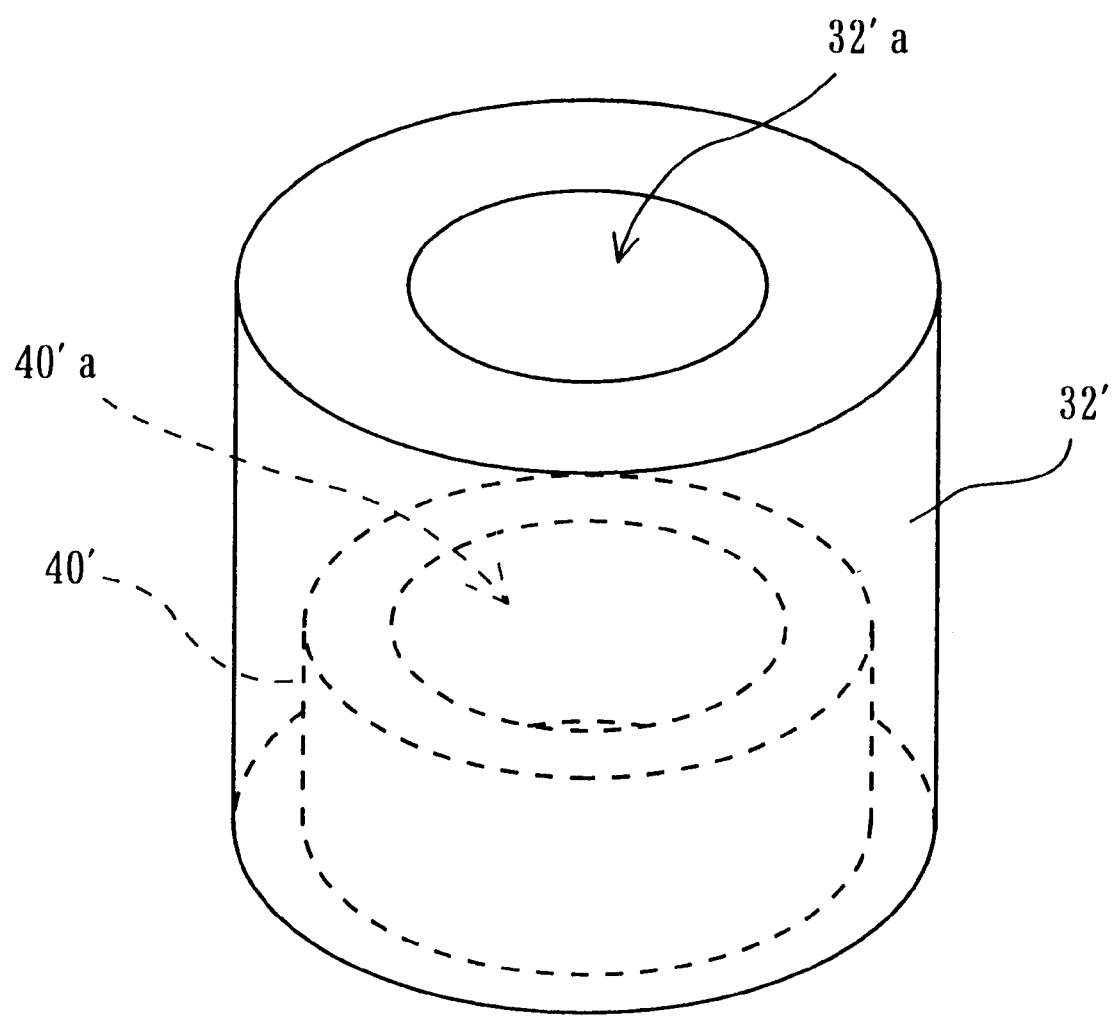
FIG. 17 is an illustrative view showing another example of the ultrasonic probe.

If an ultrasonic probe 32' as shown in FIG. 17 is employed, it is possible to perform drilling after detecting the lateral locking hole 4 without removing the ultrasonic probe 32'. That is, if utilizing a cylindrical ultrasonic probe 32' whose oscillator has an inner diameter greater than the diameter of the thread screw, a peak value can be detected in the echo from around the lateral locking hole 4 of the intramedullary nail 3 so as to specify the position at which the peak value is obtained as a point of inserting the thread screw into the lateral locking hole 4. By doing so, the thread screw is inserted in the lateral locking hole 4 while leaving the ultrasonic probe 32' mounted on the guide level 25.

The ultrasonic probe 32' shown in FIG. 17 includes a cylindrical housing that has, as a whole, a hollow portion 32'a, and accommodates a generally donut-form ultrasonic transceiver (oscillator) 40' in an internal lower portion thereof. The hollow portion 32'a and a hollow portion 40'a are preferably concentric circular, wherein the inner diameter of the hollow portion 32'a and the inner diameter of the hollow portion 40'a are both set greater than the diameter of the drill and the diameter of the set screw. The ultrasonic probe 32' is arranged to transmit an ultrasonic wave downward to receive an reflected ultrasonic wave from below thereof.

The ultrasonic probe 32' thus constructed is mounted on the lower end of the support lever 26 shown in FIG. 3, to detect the level of echo while rotating the screw 42. The position of the lateral locking hole 4 is determined by detecting a peak value in the echo given from the intramedullary nail 3 (FIG. 18). Thereafter, a hole is opened in the bone by using a drill (not shown) from the above of the skin through the support lever 26 and the guide level 25 (FIG. 3), without dismounting the ultrasonic probe 32', in a manner aiming at the femur 7 and the lateral locking hole 4 of the intramedullary nail 3. Note that, in this case, a hole for drilling is provided also through the support lever 26 located above the ultrasonic probe 32' so that the drill is lowered through the drill hole and the above-mentioned hollow portions 32'a and 40'a. Thereafter, the femur 7 and the intramedullary nail 3 are fixed through a thread screw.

If the cylindrical ultrasonic probe 32' as shown in FIG. 17 is used, the femur 7 and the intramedullary nail 3 can be accurately fixed through a thread screw while directly confirming the position of the lateral locking hole 4 by the ultrasonic probe 32.

Furthermore, the means for moving (scanning) the ultrasonic probe 32 or 32' in a direction transverse the axis of the bone (medullary cavity) is not limited to the "targeting device" by ACE Co., but an arbitrary form of a scanning means is alternatively to be utilized.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method for detecting a lateral locking hole of an intramedullary nail inserted within a medullary cavity, comprising the steps of:

(a) scanning an ultrasonic wave signal in a direction perpendicular to an axis of said intramedullary nail; and (b) detecting said lateral locking hole based on a height of an echo of said ultrasonic wave signal reflected from said intramedullary nail.

2. A method for detecting a lateral locking hole of an intramedullary nail inserted within a medullary cavity, comprising the steps of:

(a) supporting an ultrasonic probe at a location of said lateral locking hole of said intramedullary nail to be slidable in a direction perpendicular to an axis of said intramedullary nail;

(b) moving said ultrasonic probe in the direction perpendicular to an axis of said intramedullary nail; and (c) detecting said lateral locking hole based on a height of an echo of said ultrasonic wave signal reflected from the intramedullary nail.

3. An apparatus for detecting the orientation and position of a lateral locking hole of an intramedullary nail inserted within a medullary cavity, comprising:

an ultrasonic probe, said ultrasonic probe arranged to emit and detect ultrasonic signals; and a scanning means attached to said ultrasonic probe for scanning an ultrasonic signal emitted from said ultrasonic probe in a direction perpendicular to an axis of said intramedullary nail;

means for detecting the orientation and position of said lateral locking hole based on an echo obtained by said ultrasonic probe reflected from the intramedullary nail.

4. An apparatus for detecting a lateral locking hole of an intramedullary nail inserted within a medullary cavity, comprising:

an ultrasonic probe, said ultrasonic probe arranged to emit and detect ultrasonic signals; and a scanning means for scanning an ultrasonic signal emitted from said ultrasonic probe in a direction perpendicular to an axis of said intramedullary nail; said scanning means including a first support member fixed to said intramedullary nail, a second support member supported by said first support member to support said ultrasonic probe for movement in a direction perpendicular to an axis of said intramedullary nail, and a moving means for moving said second support member, whereby said lateral locking hole is detected based on an echo obtained by said ultrasonic probe reflected from the intramedullary nail.

5. A method for detecting the orientation and position of a foreign body in a bone relative to the bone, comprising the steps of:

(a) scanning an ultrasonic wave signal in a direction perpendicular to an axis of the bone; and (b) detecting the orientation and position of the foreign body relative to the bone based on a level of an echo of said ultrasonic wave signal reflected from the foreign body within the bone.

6. An apparatus for detecting the orientation and position of a foreign body in a bone relative to the bone, comprising:

an ultrasonic probe, said ultrasonic probe arranged to emit and detect an ultrasonic signal; and a scanning means attached to said ultrasonic probe for scanning an ultrasonic signal emitted from said ultrasonic probe in a direction perpendicular to an axis of the bone, means for detecting the orientation and position of the foreign body relative to the bone based on an echo obtained from said ultrasonic probe reflected from the foreign body within the bone.

7. An apparatus for detecting a foreign body within a medullary cavity, comprising:

an ultrasonic probe, said ultrasonic probe arranged to emit and detect ultrasonic signals; and a scanning means for scanning an ultrasonic signal emitted from said ultrasonic probe in a direction perpendicular to an axis of said medullary cavity; said scanning means including a first support member fixed at a predetermined axial location of said medullary cavity, and a second support member supported by said first support member to support said ultrasonic probe for movement in a direction perpendicular to an axis of said medullary cavity, and a moving means for moving said second support member, whereby the foreign body is detected based on an echo obtained from said ultrasonic probe reflected from the foreign body within the medullary cavity.

8. An ultrasonic probe arranged to transmit an ultrasonic wave signal to a medullary cavity and receive an echo of said ultrasonic wave signal from the medullary cavity to detect a lateral locking hole of an intramedullary nail within the medullary cavity, said hole being formed by a drill, into which hole a screw is inserted, comprising:

a cylindrical housing having a first hollow portion having an inner diameter greater than said drill;

a donut-form ultrasonic transceiver accommodated within said cylindrical housing and having a second hollow portion having an inner diameter greater than said screw.

* * * * *